United States Patent
Wolf et al.

(10) Patent No.: US 6,238,407 B1
(45) Date of Patent: May 29, 2001

(54) SAFETY SHIELDED REUSABLE TROCAR

(75) Inventors: Philip L. Wolf; William T. Cox, II, both of San Antonio, TX (US)

(73) Assignee: NeoSurg Technologies, Inc., Houston, TX (US)

( * ) Notice: Subject to any disclaimer, the term of this patent is extended or adjusted under 35 U.S.C. 154(b) by 1254 days.

(21) Appl. No.: 08/541,013

(22) Filed: Oct. 11, 1995

Related U.S. Application Data

(63) Continuation of application No. 08/117,233, filed on Sep. 7, 1993, now abandoned.

(51) Int. Cl.[7] .................................................. A61B 17/34
(52) U.S. Cl. .................................................. 606/185
(58) Field of Search ........................... 606/185; 604/164, 604/167, 169, 165

(56) References Cited

U.S. PATENT DOCUMENTS

| | | | |
|---|---|---|---|
| 3,097,646 | 7/1963 | Scislowicz | 128/214 |
| 3,097,647 | 7/1963 | Roehr | 128/221 |
| 3,313,299 | 4/1967 | Spademan | 128/214 |
| 3,454,006 | 7/1969 | Langdon | 128/214 |
| 3,613,684 | 10/1971 | Sheridan | 128/347 |
| 3,989,049 | 11/1976 | Yoon | 128/326 |
| 3,994,287 | 11/1976 | Turp et al. | 128/6 |
| 4,177,814 | 12/1979 | Knepshield et al. | 128/348 |
| 4,254,762 | 3/1981 | Yoon | 128/4 |
| 4,535,773 | 8/1985 | Yoon | 604/51 |
| 4,601,710 | 7/1986 | Moll | 604/165 |
| 4,654,030 | 3/1987 | Moll | 604/165 |
| 4,931,042 | * 6/1990 | Holmes et al. | 604/164 |
| 5,030,206 | * 7/1991 | Lander | 604/164 |

OTHER PUBLICATIONS

Co–pending application to Cox II, et al. assigned Ser. No. 08/663,656, entitled "A Trocar Obturator Including A Removable Knife", and filed Jun. 14, 1996.

Co–pending application to Wolf, et al. assigned Ser. No. 08/659,421, entitled "A Trocar Including An Obturator With A Removable Knife", and filed Jun. 6, 1996.

"Product Directory", Surgeons' Reference™ For Minimally Invasive Surgery Products™, 2nd Edition, Sep. 1995, pp. 11–202—11–223.

\* cited by examiner

*Primary Examiner*—Michael H. Thaler
(74) *Attorney, Agent, or Firm*—McGlinchey Stafford; Clarence E. Eriksen

(57) ABSTRACT

A safety shielded, reusable trocar consisting of a trocar cannula subassembly, a safety shield control mechanism, and a separate obturator subassembly. The trocar cannula subassembly includes an outer cannula attached to a main housing having a central bore in which a spring biased, inner cannula is slidably and removably inserted, and an upper housing, removably secured to the main housing, having a central bore which is aligned longitudinally with the bore of the main housing and in which a seal is removably secured. The obturator subassembly includes an elongated obturator having a replaceable and rotatable knife, an elongated shaft, an arcuate shaped cap, and which extends through the upper housing, seal, main housing, inner cannula, and outer cannula. The safety shield control mechanism, located in the main housing and removably engaged with the inner cannula, allows for positive and easily verifiable engagement and disengagement of the inner cannula as a safety shield for the obturator knife. When the trocar cannula subassembly and safety shield control mechanism are coupled proper operation of the safety shield can be verified without the obturator subassembly being inserted in the inner cannula. In operation, the obturator subassembly, upper housing, and a seal can be completely removed from the trocar assembly to allow unobstructed access through the inner cannula to the patient's internal cavity for removal of specimens or insertion of equipment. After use, the entire trocar assembly can be easily disassembled for cleaning, sterilization, and reuse.

7 Claims, 7 Drawing Sheets

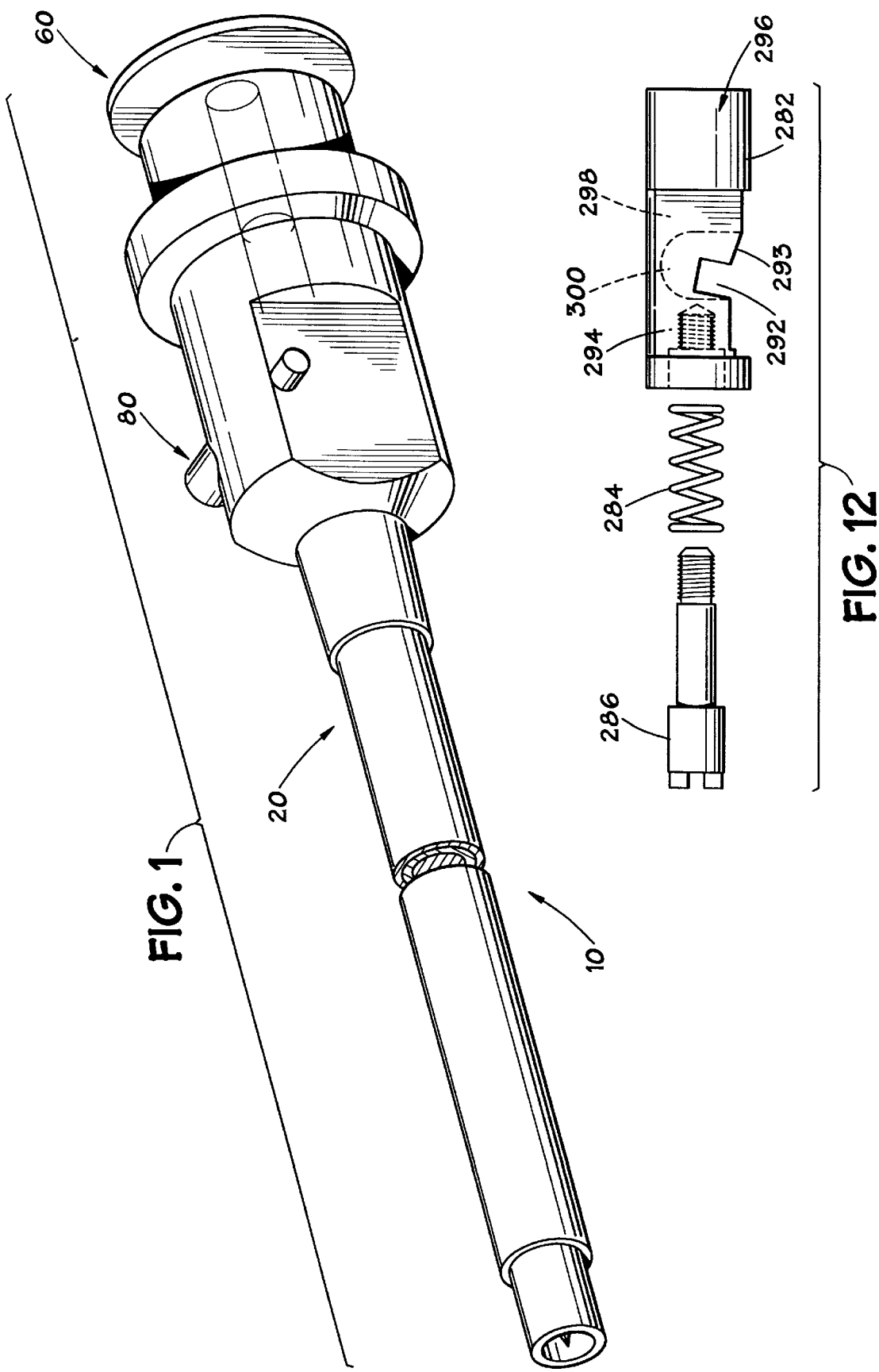

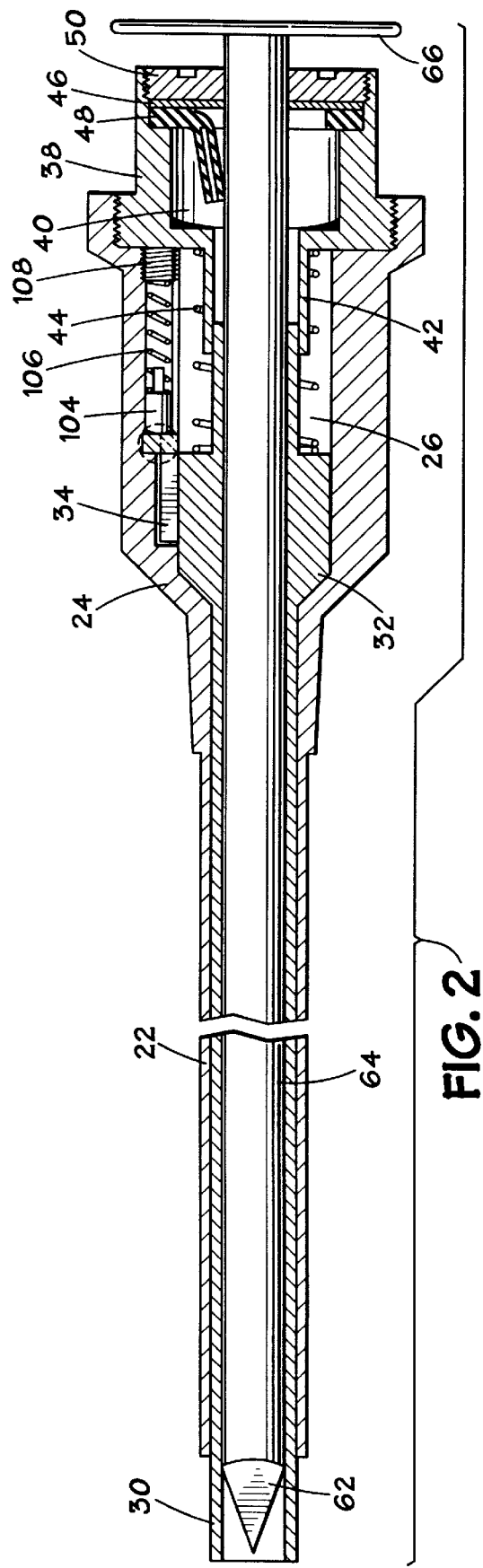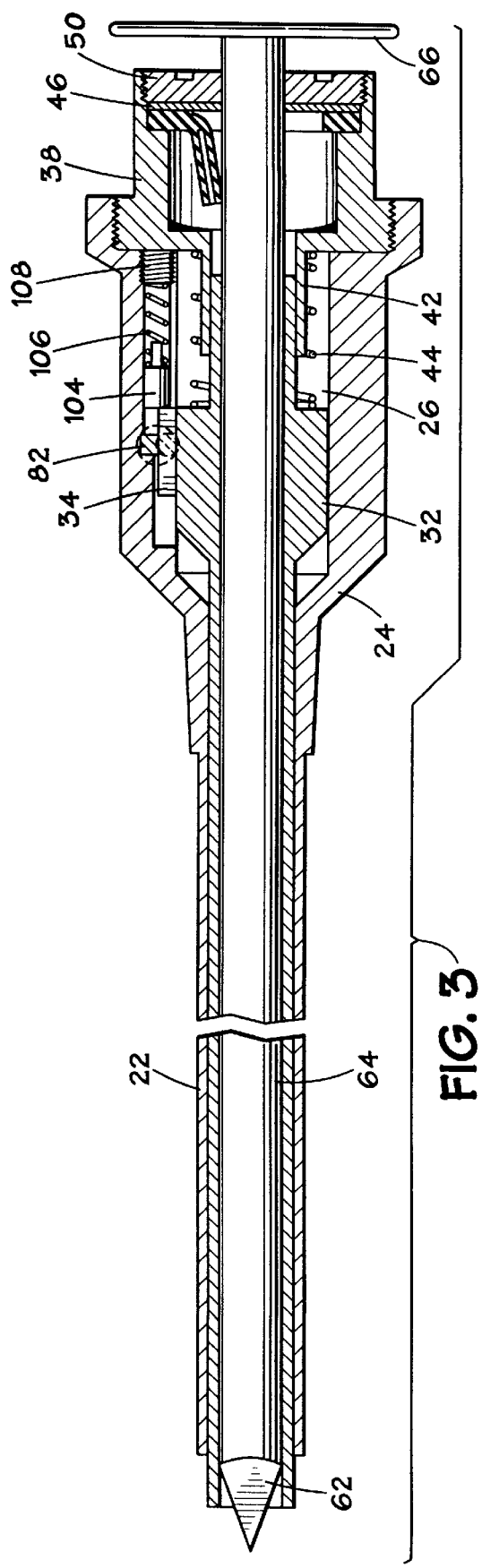

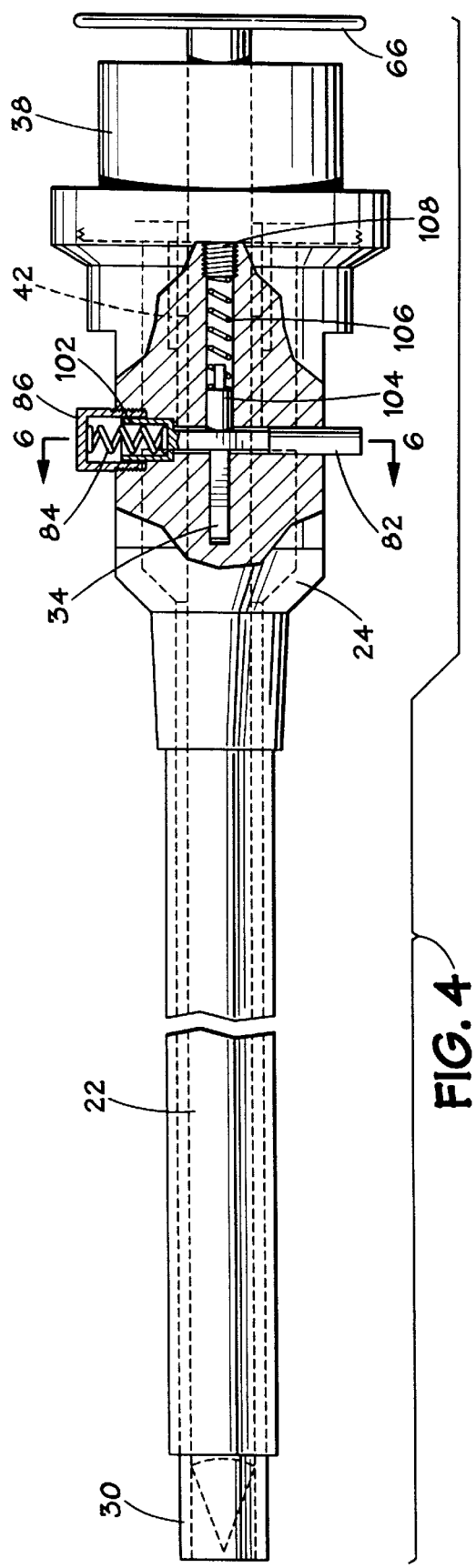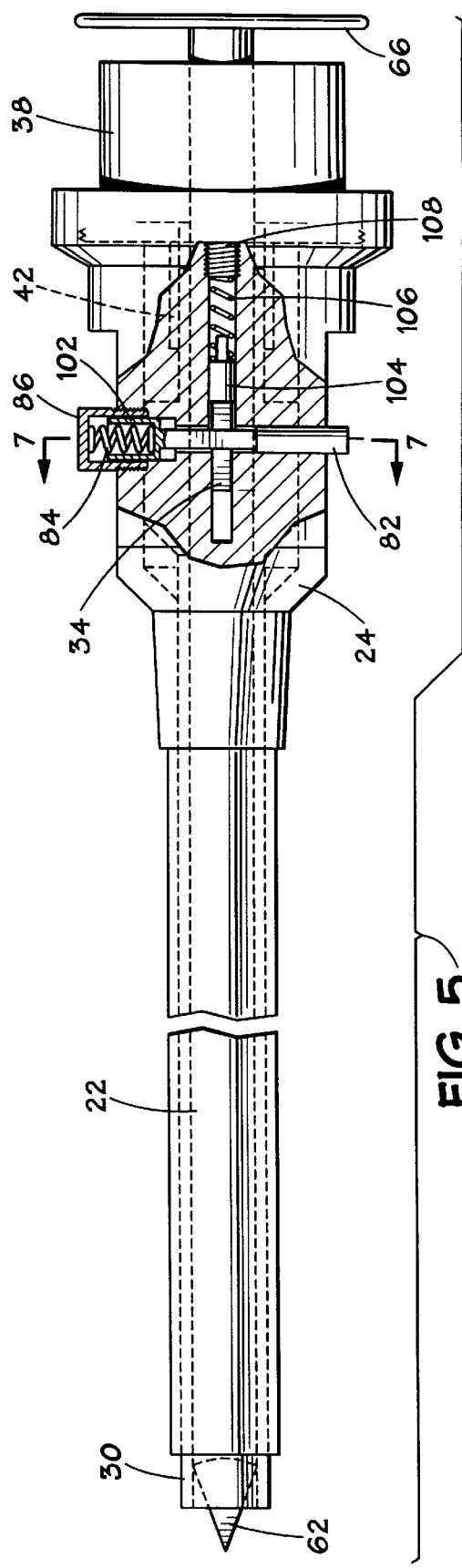

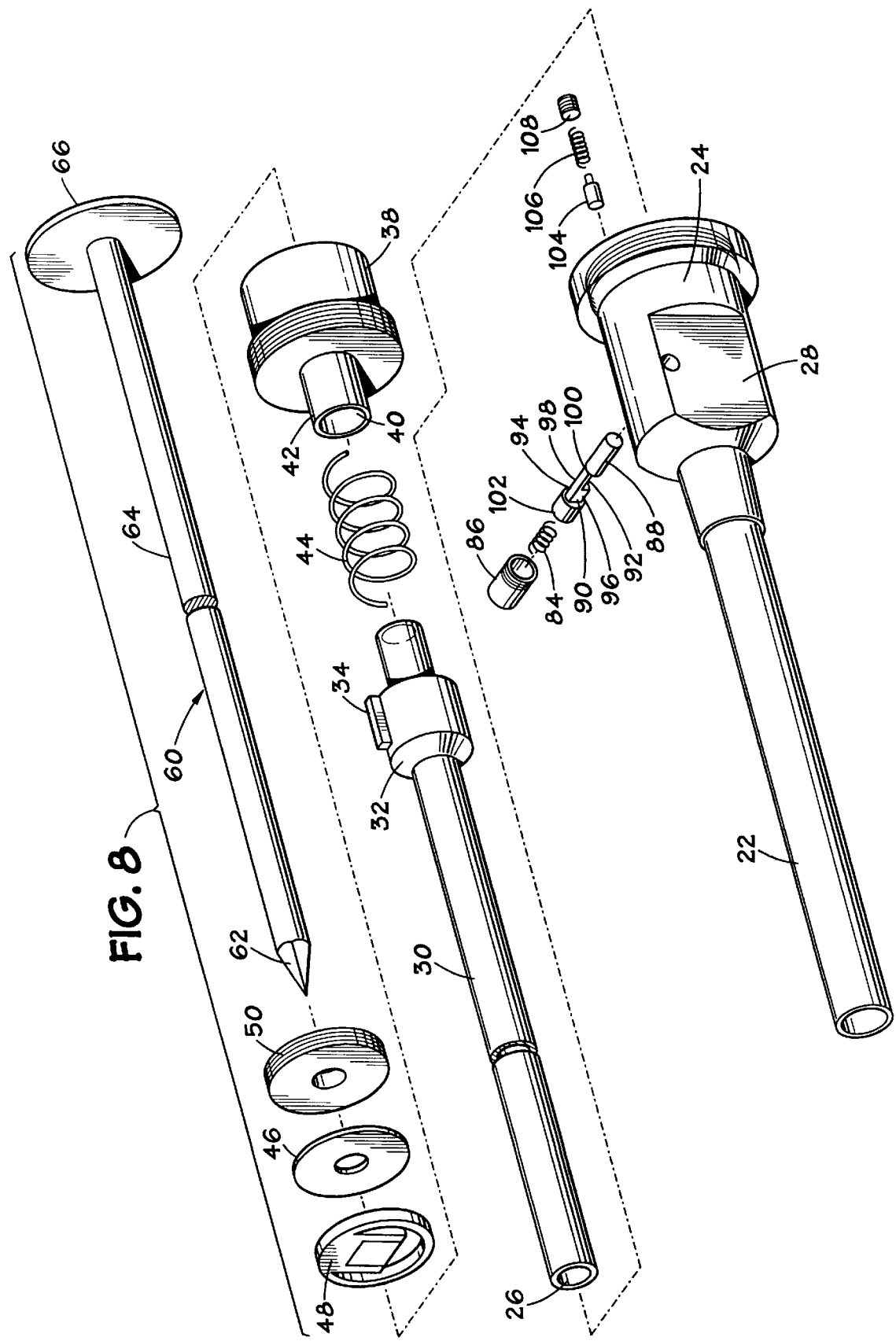

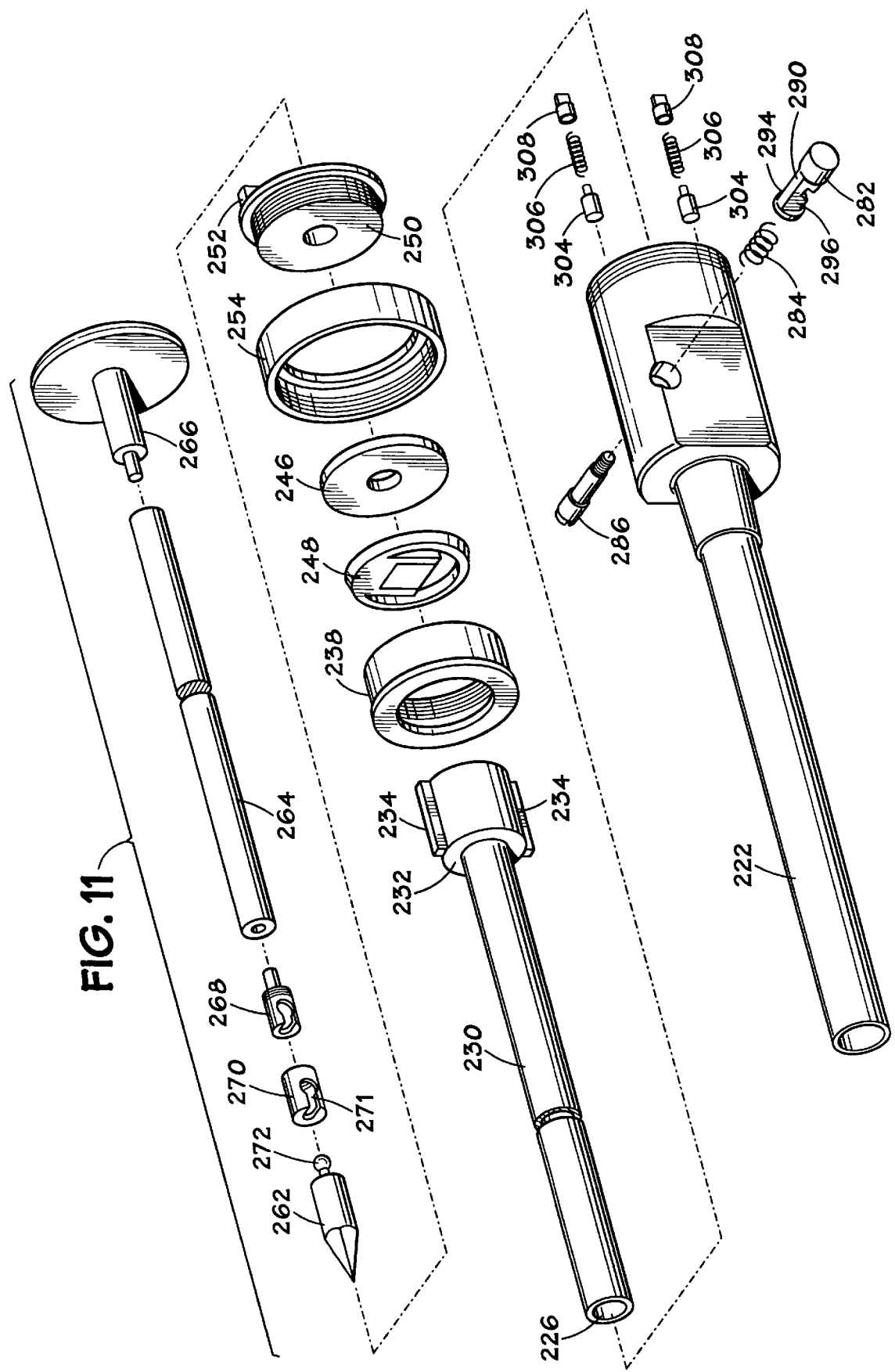

SAFETY SHIELDED REUSABLE TROCAR

CROSS-REFERENCE TO RELATED APPLICATIONS

This application is a continuation of application Ser. No. 08/117,233 filed on Sep. 7, 1993, now abandoned.

BACKGROUND OF THE INVENTION

1. Field of the Invention

Applicant's invention relates to surgical instruments and, more particularly, to trocars. Trocars are used to pierce or puncture an anatomical cavity to provide communication with the inside of the cavity during a surgical procedure.

2. Background Information

Endoscopic surgery, particularly laparoscopic surgery, is currently becoming a significant method for performing surgeries. It is projected that by the year, 2000 half of all surgical procedures will be performed endoscopically. Laparoscopic surgery has become the surgical procedure of choice because of its patient care advantages over "open surgery."

For the past several decades, endoscopic surgery has been available as a method of diagnosis and, for a very limited number of disorders, a treatment. Until recently, a factor limiting the types of surgeries that could be performed laparoscopically was the ability to employ intraoperative assistance. In the past, endoscopes allowed only direct visualization by the surgeon, such as the endoscope disclosed in U.S. Pat. No. 4,254,762 issued to Yoon. This led to the situation where the surgeon had one hand holding the laparoscope to his eye and then had only one hand available to operate.

Fortunately, miniaturization of video camera computer chips has led to the development of video cameras that can easily be attached to an endoscope or laparoscope. During surgery, connecting a video camera and monitor to the laparoscope enables all the operating room personnel to view the surgical procedure, rather than just the surgeon. Thus, the operating room personnel are able to provide operative assistance just as they do with open surgery. The type and number of surgical procedures amenable to laparoscopic surgery is presently one of the most rapidly developing areas of medicine.

The pivotal advantage of laparoscopic surgery over open surgery is the decreased post-operative recovery time. In many instances, a patient is able to leave the hospital within twenty four hours after laparoscopic surgery has been performed. This is compared to a five day to ten day hospitalization necessary to recover from an open surgical procedure. Additionally, laparoscopic surgery provides a decreased incidence of post-operative abdominal adhesions and decreased post-operative pain with enhanced cosmetic results.

An essential medical instrument for endoscopic procedures is the trocar. Trocars are sharp, pointed surgical instruments used to puncture the wall of an anatomical cavity. The trocar consists of a tube or cannula and a cutting element called an obturator or stylet. The obturator fits within the cannula and has a sharp piercing tip at its end.

A conventional laparoscopic trocar insertion procedure usually follows insufflation of the abdominal cavity with $CO_2$ gas. The introduction of $CO_2$ gas into the abdominal cavity lifts the abdominal wall away from the internal viscera. Once this is done, the abdominal wall is penetrated with the trocar. After insertion of the trocar through the abdominal wall, the surgeon removes the obturator leaving the cannula or tube protruding through the body wall. A laparoscope or laparoscopic instruments can then be inserted through the cannula to view internal organs or perform surgical procedures.

Penetrating the wall of the abdominal cavity with the trocar is done quickly. The sharp point of the obturator encounters great resistance from the skin, muscle, and tissue membranes of the abdominal wall while it is being pushed through these structures. Once the trocar's sharp point and blade pass through the abdominal wall and into the cavity, the resistance to the trocar drops quickly. Unless the surgeon immediately stops pushing the trocar just as soon as penetration of the abdominal wall is complete, there is a chance that the trocar will penetrate further into the abdominal cavity and injure internal organs.

Within the abdominal cavity, the obturator's sharp point could easily injure or cut an internal organ upon the slightest contact. If an internal organ is inadvertently injured or cut, unless immediate and massive hemorrhage occurs, the injury may not become apparent until long after completion of the surgery. At a minimum, such an injury will delay a patient's recovery and, more likely, could seriously endanger the patient's health. Additional corrective surgery on an open basis may be required, subjecting the patient to additional risks and costs.

Prior to 1987, the only trocars available for laparoscopic use were instruments made from stainless steel, such as those disclosed in U.S. Pat. No. 3,994,287 issued to Turp et al., and U.S. Pat. No. 3,613,684 issued to Sheridan. A problem common to all of these "classic" trocars is that they do not have a safety shield which covers the sharp, cutting tip of the obturator once it pierces the cavity wall.

Several changes and additions have been made on the functional design of these classic trocars. The most significant improvement on the classic trocar is the addition of a spring-loaded safety shield that snaps forward to cover the sharp point and blade of the obturator once the trocar has penetrated the abdominal wall, such as those disclosed in U.S. Pat. No. 4,601,710 issued to Moll, U.S. Pat. No. 4,654,030 issued to Moll et al. and U.S. Pat. No. 4,535,773 issued to Yoon. In these devices, the safety shield is a plastic sleeve which is positioned concentrically about the obturator. Because of this safety feature, trocars with a spring loaded safety shield have become the most used trocars in laparoscopic surgery.

However, these spring loaded safety shields have cumbersome safety shield control mechanisms which are difficult to tell if the safety shield is armed or engaged. To be sure of the safety shield's operation, a surgeon will need to verify the proper operation of the safety shield prior to use. Since the safety shields are mounted to the obturator, surgeons are required to test the safety shield's operation with the obturator in place by manually pressing the safety shield of the trocar. Unfortunately, this results in many slight puncture wounds being experienced by the surgeons as they are attempting to verify the safety shield's operation.

Currently, laparoscopic trocars with the spring loaded safety shields are manufactured only as a thin wall plastic disposable instruments. These light weight plastic instruments are used once and then discarded as medical waste, adding significantly to the already escalating health care costs. For example, the single use disposable plastic trocars cost approximately sixty five dollars to ninety dollars each. Usually two to four trocars are used for each laparoscopic procedure. Thus, surgical costs are unnecessarily increased about two hundred dollars to three hundred and fifty dollars per laparoscopic procedure, as well as adding to the overbearing problem of medical waste by the use of these disposable trocars. Presently, however, the increased health care cost has been unavoidable because the only safety shielded trocar available was a disposable item. No one had invented a easily disassembled, easily cleaned, sterilized, and easily reassembled for reuse, safety shielded trocar.

SUMMARY OF THE INVENTION

Accordingly, it is an object of the present invention to provide a safety shield which can be tested for proper operation without the obturator being located in the cannula.

It is another object of the present invention to provide a safety shield control mechanism which is easy to verify if the safety shield is armed or safe.

It is further object of the present invention to provide a safety shield which is removable and separate from the obturator.

It is still another object of the present invention to provide a reusable trocar with a safety shield which is easily disassembled, easily cleaned, sterilized, and easily reassembled for reuse.

It is yet another object of the present invention to provide a trocar in which the upper housing can be quickly disassembled from the main housing while in use to allow for unobstructed access through the trocar to the body cavity.

An additional object of the present invention is to provide a means by which the trocar blade or cutting tip can be easily replaced after each surgical procedure thus providing a sharp cutting edge for each surgical use and also minimizing medical waste.

These and other objects are met by Applicant' invention of a safety shielded, reusable trocar consisting of a trocar cannula subassembly, a safety shield control mechanism, and a separate obturator subassembly. The trocar cannula subassembly includes an outer cannula attached to a main housing having a central bore in which a spring biased, inner cannula is slidably and removably inserted, and an upper housing, removably secured to the main housing, having a central bore which is aligned longitudinally with the bore of the main housing and in which sealing means is removably secured.

The obturator subassembly includes an elongated obturator having a replaceable and rotatable knife, an elongated shaft, an arcuate shaped cap, and which extends through the upper housing, sealing means, main housing, inner cannula, and outer cannula.

The safety shield control mechanism, located in the main housing and removably engaged with the inner cannula, allows for positive and easily verifiable engagement and disengagement of the inner cannula as a safety shield for the obturator knife. When the trocar cannula subassembly and safety control mechanism are coupled proper operation of the safety shield can be verified without the obturator subassembly being inserted in the inner cannula.

In operation, the obturator subassembly, upper housing, and sealing means can be completely removed from the trocar assembly to allow unobstructed access through the inner cannula to the patient's internal cavity for removal of specimens or insertion of equipment. After use, the entire trocar assembly can be easily disassembled for cleaning, sterilization, and reuse.

The foregoing will become apparent from the following detailed description of a preferred embodiment with reference to the accompanying figures.

BRIEF DESCRIPTION OF THE DRAWINGS

FIG. 1 is a perspective view of the present invention.

FIG. 2 is a cross sectional view of the present invention with the safety shield extended.

FIG. 3 is a cross sectional view of the present invention with the safety shield partially retracted.

FIG. 4 is a cut-away sectional view of the present invention showing the trigger in the safe position.

FIG. 5 is a cut-away sectional view of the present invention showing the trigger in the armed position.

FIG. 8 is an exploded view of the present invention.

FIG. 11 is an exploded view of an alternative embodiment of the present invention.

FIG. 12 is an exploded view of the trigger mechanism of the alternative embodiment shown in FIG. 11.

DETAILED DESCRIPTION OF THE PREFERRED EMBODIMENT

Figure 7:
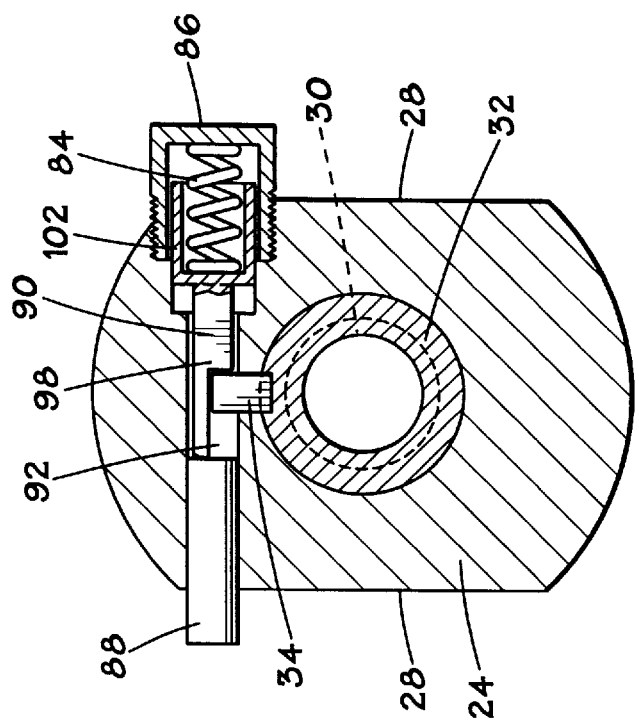
FIG. 7 is a cross sectional view of the present invention taken along line 7—7 of FIG. 5.

Referring now to the drawings, FIGS. 1–8 illustrate a first embodiment of a safety shielded, reusable trocar generally designated (10) consisting of a trocar cannula subassembly (20), a safety shield control mechanism (80), and a separate obturator subassembly (60). The three subassemblies are interfitting, but are designed to be easily disassembled for easy cleaning and sterilizing. To facilitate the reusable features of the trocar (10), it is preferably made from a durable and strong material which can be cleaned and sterilized, such as surgical stainless steel, acetal, polysulfone, or any high temperature thermoplastic. However, any material is acceptable as long as it may be sterilized by gas, autoclave, cold sterilization, and the like.

Referring to FIG. 8, the trocar cannula subassembly (20) includes an outer cannula (22) attached to a main housing (24). The outer cannula (22) may be attached to the main housing (24) in a variety of different methods including the outer cannula (22) being pressed on to the main housing (24) or it may be machined out of the same piece of metal as the main housing (24). The outer cannula (22) and main housing (24) align to have a central axial bore (26) for receiving the inner cannula (30) and the obturator subassembly (60). The central axial bore (26) is larger in the main housing (24) than in the outer cannula (22). Main housing (24) has rectangular recesses (28) to facilitate gripping the trocar with the fingers and for quickly locating the safety shield control mechanism (80).

The inner cannula (30) is a tube adapted to be slidably inserted into outer cannula (22) and main housing (24) and serves as a safety shield for the obturator subassembly (60). The aft end of the inner cannula (30) has a slider (32) attached which is adapted to allow smooth sliding of the inner cannula (30) in the larger central axial bore of the main housing (24). The slider (32) also serves as a stop to prevent inner cannula (30) from sliding completely through main housing (24). The rear end of slider (32) has an elongated key (34). The inner side of main housing (24) has a keyway (not shown) in which key (34) rides to permit axial movement without rotation of the inner cannula (30) relative to the outer cannula (22) and main housing (24).

As shown in FIGS. 2 and 8, upper housing (38) is removably secured to main housing (24). Upper housing (38) has a lower tube (42) with a central axial bore (40) adapted to receive the rear end of inner cannula (30). A spring (44) sits around the rear end of the inner cannula (30) and lower tube (42) with its ends seated against the bottom of upper housing (38) and the top of slider (32). Spring (44) biases inner cannula (30) in the extended position. The bottom of lower tube (42) serves as a stop to limit the rearward axial movement of inner cannula (30) relative to main housing (24).

Upper housing (38) houses removable sealing means including a removable, upper wiper seal (46) and a removable flapper valve seal (48). The seals are preferably made of durable silicon rubber and plastic which can be sterilized. Wiper seal (46) has a central opening which is approximately equal to the outside diameter of obturator. The primary function of wiper seal (46) is to insure a tight seal when the stem or shaft of obturator or other instrument shafts are inserted through upper housing (38). Flapper valve (48) acts as a closure means when obturator or other instrument is withdrawn and separated from the trocar cannula subassembly (20). Sealing means retainer (50) is removably attached to upper housing (38) and serves as a keeper of the seals to prevent them from falling out of upper housing (38). Sealing means retainer (50) has a central bore longitudinally aligned with the central bore of inner cannula (30) for receiving the shaft of obturator or other instrument.

The obturator subassembly (60) includes a pyramidal-shaped knife (62), an elongated stem or shaft (64), an arcuate shaped cap (66). Obturator (60) is adapted to extend and move longitudinally through upper housing (38), main housing (24), outer cannula (22), and inner cannula (30). Inner cannula (30) serves as a safety shield for the knife (62) portion of obturator (60). Obturator (60) may be easily removed from the trocar cannula subassembly (20).

The operation of the inner cannula (30) is controlled by the safety shield control mechanism (80) which is removably located in the main housing (24) and is removably engaged with the inner cannula (30). Safety shield control mechanism (80) provides visual, tactile, and aural signals to the operator allowing for positive and easily verifiable engagement and disengagement of the inner cannula (30) as a safety shield for the obturator knife (62). When the trocar cannula subassembly (20) and safety shield control mechanism (80) are coupled, proper operation of the safety shield can be verified without the obturator subassembly (60) being inserted in the inner cannula (30).

As shown in FIGS. 2 through 7, the safety shield control mechanism (80) includes a trigger pin (82), trigger spring (84), and red pin (86) which extend perpendicularly through a chamber in the main housing (24). Red pin (86) is removably secured to main housing (24). The ends of trigger spring (84) are seated against the inner face of red pin (86) and the inner face of trigger pin (82) biasing trigger pin (82) in an extended position.

Trigger pin (82) has a finger (88) which extends perpendicularly from main housing (24). Secured to finger (88) is an offset rectangular member (90) having a keyway (92) and an upper face (94) and a lower face (96). Upper face (94) has two steps (98 and 100). Secured to offset rectangular member (90) is a circular housing (102) for receiving trigger spring (84).

Also part of the safety shield control mechanism (80) are a latch pin (104), a latch spring (106), and a latch spring retainer (108) located in the same keyway in main housing (24) as key (34). Latch pin (104) is adapted to abut key (34) to assist in spring biasing inner cannula (30) to the extended position.

Figure 6:
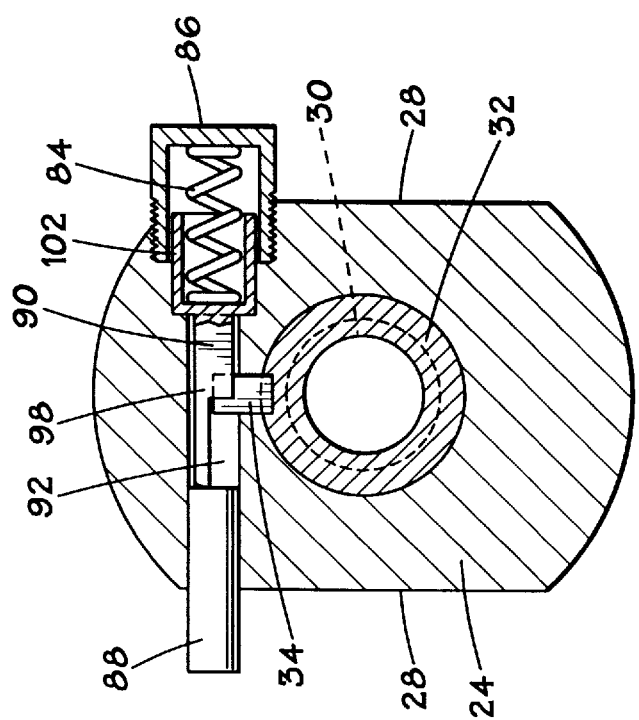
FIG. 6 is a cross sectional view of the present invention taken along line 6—6 of FIG. 4.

In the safe position as shown in FIGS. 2 and 6, trigger pin (82) is trigger spring (84) biased in the extended position so that latch pin (104) is demountably located on the first step (98) of upper face (94) of offset rectangular member (90) and lower face (96) of offset rectangular member (90) prevents key (34) from moving axially rearward, thereby keeping the safety shield extended and locked over obturator knife (62).

To arm, as shown in FIG. 7, trigger pin (82) is pushed in perpendicularly to main housing (24) a sufficient distance to allow latch spring (106) biased latch pin (104) to drop to the second step (100) of upper face (94). Latch pin (104) while on the second step (100) abuts the side of the first step (98) and serves as a latch to prevent perpendicular movement by trigger spring (84) biased trigger pin (82) and keeps trigger pin (82) in the armed position. With trigger pin (82) in the armed position, keyway (92) of offset rectangular member (90) is aligned with key (34) of inner cannula (30) thereby allowing inner cannula (30) to move longitudinally inside outer cannula (22). When inner cannula (30) moves rearward, as shown in FIG. 3, key (34) lifts latch pin (104) and trigger pin (82) is trigger spring (84) biased outward towards the safe position. As inner cannula (30) moves forward, key (34) moves past trigger pin (82) and first step (98) of offset rectangular member (90) engages latch pin (104), thereby putting safety shield control mechanism (80) in the safe position.

The safety shielded, reusable trocar (10) operates and is used as follows. Before use the trocar (10) will typically be in the assembled form as shown in FIGS. 1 and 2 with the inner cannula (30) locked in position as a safety shield for the obturator for safety purposes and for storage. In this position the knife (62) or piercing tip is shielded and cannot be damaged by inadvertent contact with other surfaces. In this locked position, spring (44) biases inner cannula (30) forward with the forward edges of slider (32) acting as stops against the lower, inner portion of main housing (24) to define the forwardmost position of inner cannula (30). Also in this locked position, lower face (96) of trigger pin (82) acts as stops against the rearward edges of slider (32) to define the rearmost position of inner cannula (30) and trigger pin (82) is in its extended position as shown in FIGS. 4 and 6. Flapper valve (48) is biased against the shaft (64) of obturator (60) to frictionally minimize longitudinal movement of obturator (60) relative to main housing (24). The inner lip of wiper seal (46) rests snugly against the shaft (64) of obturator (60) and forms a seal therewith.

To unlock inner cannula (30) from its safety shield position, trigger pin (82) is pushed in perpendicularly to main housing (24), as shown in FIGS. 5 and 7. Latch pin (104) moves to the second step (100) of trigger pin (82) and keyway (92) of trigger pin (82) is aligned with key (34) of inner cannula (30). When latch pin (104) moves to the second step (100) of trigger pin (82) an audible click is heard by the operator. In this armed position, inner cannula (30) is free to move longitudinally rearward until stopped by slider (32) abutting the lower tube (42) of upper housing (38).

In surgical use, the trocar (10) is used in conjunction with insufflatory techniques wherein a needle type instrument first punctures the skin in a desired body cavity region.

Usually, the needle house a stylet or the like that introduces a gas like carbon dioxide from a pressurized container into the body cavity. After the cavity has been inflated, a small incision may be made in the skin at the desired body cavity location. The trocar (10) is put in its armed position. The trocar (10) is gripped firmly with the cap (66) of the obturator (60) against the palm of the surgeon's hand. The safety shield portion of the inner cannula (30) is placed against the incision in the skin and firm pressure is exerted against the skin. The pressure causes the inner cannula (30) to be pushed rearwardly against spring (44) to its retracted position as shown in FIG. 3, thereby exposing the knife (62) of the obturator, and key (34) lifts latch pin (104) from the second step (100) of trigger pin (82). The tip of the knife (62) enters the incision and underlying tissue with continued pressure.

Once the knife (62) has penetrated tissue and has entered the cavity, the force against the front end of the inner cannula (30) ceases and the inner cannula (30) is automatically moved longitudinally back to its extended position through the action of spring (44). As inner cannula (30) moves forward, key (34) moves past trigger pin (82) and first step (98) of offset rectangular member (90) engages latch pin (104), thereby putting safety shield control mechanism (80) in the safe and locked position.

The obturator subassembly (60) may be withdrawn from the trocar cannula subassembly (20) once the cavity has been penetrated. During withdrawal, once the tip of the obturator (60) clears the opening in wiper seal (46), flapper valve (48) will bias the flapper to a sealed position. Air pressure within the body cavity is thus maintained. Although not shown, main housing (24) may include a stopcock port into which the nozzle of a stopcock could be inserted to pass additional insufflating gas into the cavity.

The trocar will normally be inserted into the body cavity until main housing (24) abuts the skin. After the obturator subassembly (60) has been separated from the trocar cannula subassembly (20), surgical instruments may be inserted into the body cavity via the central bore (26) of trocar cannula subassembly (20) to view internal tissues, perform operations thereon, or drain bodily fluids.

If the surgeon desires obstructed access to the body cavity for better viewing or to take a tissue sample, upper housing (38) may be removed from main housing (24). By removing upper housing (38), the wiper seal (46), flapper seal, and seal retainer (50) are all removed as a single unit. The trocar cannula subassembly (20) then provides unobstructed access to the body cavity to permit removal of specimens and to deflate the cavity.

After use, the entire trocar (10) can be easily disassembled for cleaning, sterilization, and ready for reuse. Sterilization can be by any standard sterilization technique.

An alternative embodiment of the present invention is illustrated in FIGS. 9–12.

Although the function and operation of the safety shielded, reusable trocar are the same, there are slight changes to each subassembly unit.

The trocar cannula subassembly (220) includes an inner cannula (230) having a slider (232) located flush with the rearmost end of the inner cannula (230). A pair of diametrically opposed axially elongated keys (234) are attached to slider (232). The interior of main housing (224) has complementary keyways (not shown) for receiving keys (234) and allowing longitudinal movement of inner cannula (230) without any rotational movement of inner cannula (230) relative to main housing (224) and outer cannula (222). A pair of diametrically opposed latch spring mechanisms are removably located in keyways. Latch spring mechanisms include a latch pin (304), latch spring (306), and a latch spring retainer (308). Latch spring mechanisms are adapted to abut keys (234) to spring bias inner cannula (230) to the extended position. The interaction between the latch spring mechanism, trigger pin (282), and keys (234) is as described above for the first embodiment of the present invention.

Figure 9:
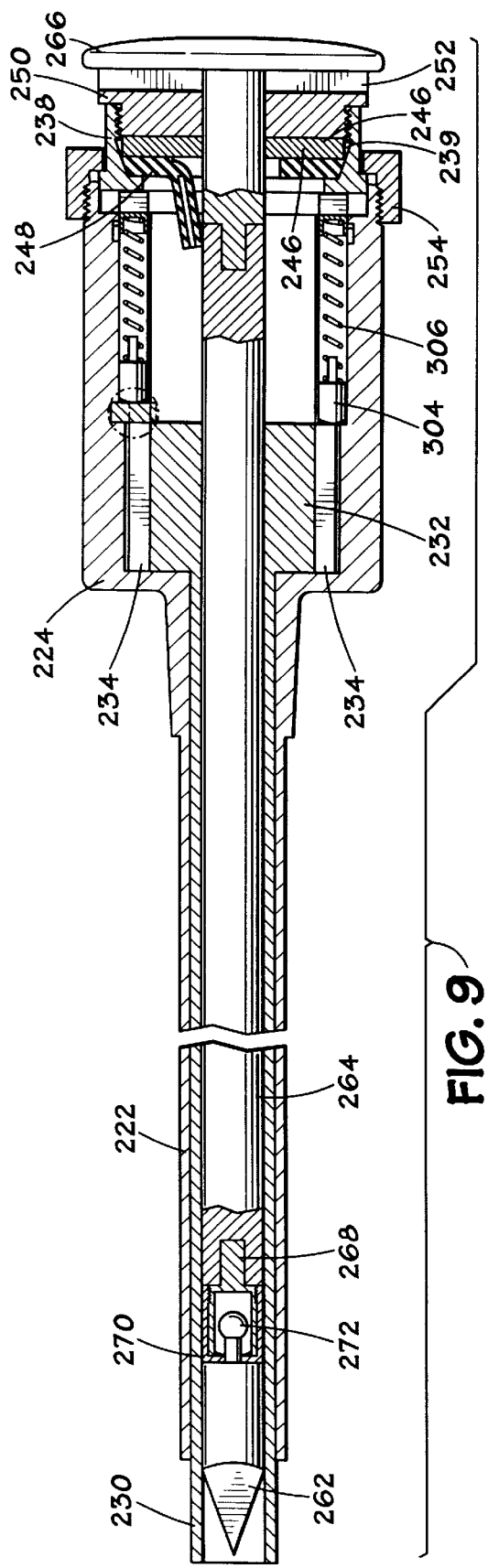
FIG. 9 is a cross sectional view of the alternative embodiment shown in FIG. 11 with the safety shield extended.
Figure 10:
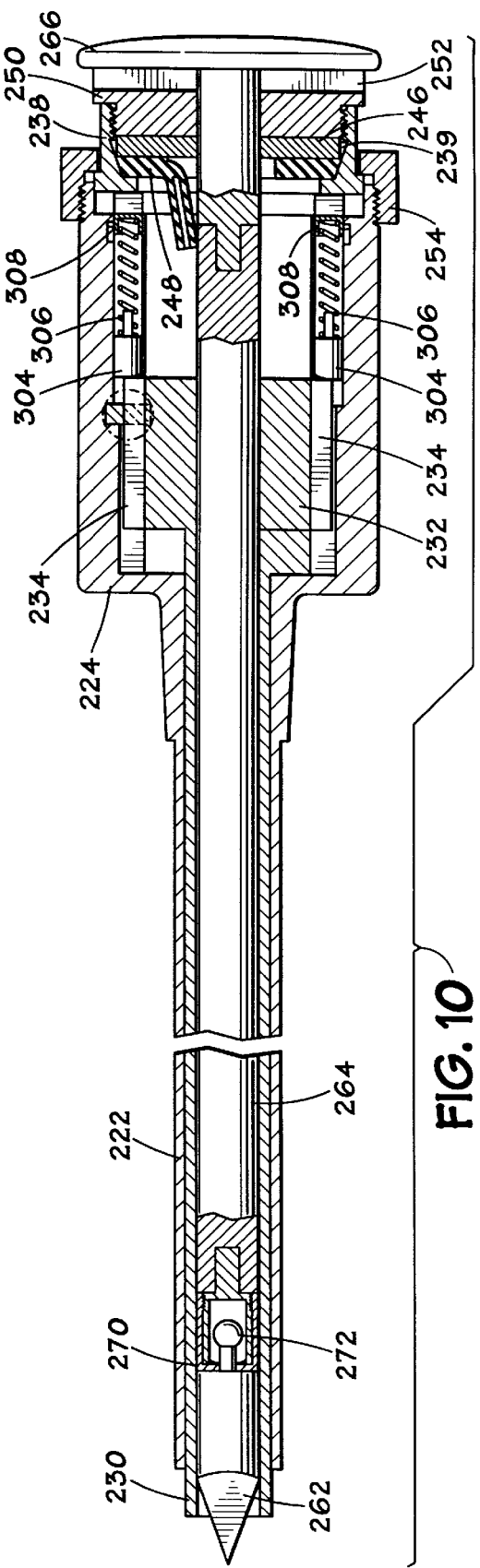
FIG. 10 is a cross sectional view of the alternative embodiment shown in FIG. 11 with the safety shield partially retracted.

Upper housing (238) has a bevelled interior surface (239) to house sealing means such as a flapper valve (248) and wiper valve (246). The edges of flapper valve (248) are complementarily bevelled so that the sealing means can only be inserted with flapper valve (248) closest to inner cannula (230). If the sealing means would be reversed, the sealing means would not fit into upper housing (238). Sealing means are kept in place by a sealing means retainer (250) having a handle (252) to provide easy removable securing to upper housing (238). Upper housing (238) is removably engaged between a lock ring (254) which couples to main housing (224), as shown in FIGS. 9 and 10.

The obturator subassembly (260) in this embodiment has a cap (266) secured to a shaft (264). To reduce the overall weight of the trocar, the shaft (264) may be made of a lightweight and durable material such as aluminum. Secured to the opposite end of shaft (264) is a capture fitting (268) for receiving the rounded end (272) of the knife (262). The knife (262) made be made of stainless steel or alternatively, to further reduce the overall weight, the knife (262) made be made of high temperature thermoplastic. This also gives the additional advantage of making the knife (262) easily replaceable and interchangeable to ensure that the knife is always sharp.

The knife (262) is rotatably and removably secured to the shaft (264) by means of a capture fitting (268) and capture nut (270) arrangement. As best seen in FIG. 11, capture fitting (268) and capture nut (270) are aligned to form a opening (271) for receiving the rounded end of the knife (262). The knife (262) is inserted sideways through opening (271). The capture nut (270) is then rotated at least thirty degrees to rotatably lock knife (262) to the shaft (264), as shown in FIG. 9.

The safety shield control mechanism (280) operates in the same manner as described above. However, the trigger pin has been modified as shown in FIGS. 11 and 12. The trigger pin (282) is now designed to move in and out of both sides of the main housing (224), much like a safety on a rifle. In the armed position, the red pin (286) protrudes from the main housing (224) and may be painted the color red. In the safe position, the trigger pin (282) protrudes from the main housing (224) and may be colored green or black. Additionally, the offset rectangular member (290) has been modified for the upper face (294) to have an arcuate shaped second step (300) and the lower face has an angled keyway (292) with a bevelled side surface (293). The bevelled side surface (293) allows for smoother pickup and dropping of the latch pin (304).

In operation of the alternative embodiment, the steps are the same as previously described. During insertion of the trocar, the knife (262) is rotatable. This facilitates a smooth incision through the skin as the rotatable knife (262) rotates to counter any rotation of the trocar by the surgeon while applying pressure to the skin.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A safety-shielded trocar, comprising:

a trocar cannula;

an inner cannula within said trocar cannula, wherein said inner cannula moves axially relative to said trocar cannula between an extended position and a retracted position;

means acting on the rear end of said inner cannula for biasing said inner cannula to its extended position;

means for locking within said trocar cannula, wherein said means for locking is movable between a first position that locks said inner cannula in its extended position and a second position that permits axial movement of said inner cannula to its retracted position; and means for latching within said trocar cannula wherein, upon the movement of said means for locking from its first position to its second position, said means for latching engages said means for locking to retain said means for locking in its second position until the axial movement of said inner cannula rearward relative to said trocar cannula disengages said means for latching from said means for locking.

2. The safety-shielded trocar according to claim 1 further comprising an obturator placeable within said trocar cannula wherein said inner cannula shields a knife edge of said obturator in its extended position and exposes the knife edge of said obturator in its retracted position.

3. The safety-shielded trocar according to claim 1 further comprising means for sealing said trocar cannula.

4. The safety-shielded trocar according to claim 3 wherein said means for sealing is removable from said trocar cannula to provide unobstructed access through said trocar cannula.

5. The safety-shielded trocar according to claim 1 wherein said trocar cannula comprises an outer cannula attached to a housing.

6. The safety-shielded trocar according to claim 1 wherein said means for locking, comprises:

a trigger mounted transversely within said trocar cannula, said trigger including a protrusion and a recess;

means for biasing said trigger to engage said inner cannula with its protrusion to prevent the movement of said inner cannula from its extended position to its retracted position; and said trigger movable to a position wherein its recess resides over said inner cannula to permit the movement of said inner cannula from its extended position to its retracted position.

7. The safety-shielded trocar according to claim 6 wherein said means for latching, comprises:

a pin that engages said trigger when said trigger is in its position wherein its recess resides over said inner cannula; and means for biasing said pin against said trigger.

* * * * *

UNITED STATES PATENT AND TRADEMARK OFFICE
CERTIFICATE OF CORRECTION

PATENT NO. : 6,238,407 B1
DATED : May 29, 2001
INVENTOR(S) : Philip L. Wolf et al.

Page 1 of 1

It is certified that error appears in the above-identified patent and that said Letters Patent is hereby corrected as shown below:

<u>Column 3,</u>
Line 34, delete "Applicant" and insert -- Applicants' --

<u>Column 8,</u>
Lines 27 and 28, after (262), delete "made" and insert -- may --
Line 48, delete "red"

Signed and Sealed this

Eighth Day of January, 2002

Attest:

Attesting Officer

JAMES E. ROGAN
*Director of the United States Patent and Trademark Office*